United States Patent [19]  [11] 4,278,679
Madison et al.  [45] Jul. 14, 1981

[54] COMBINATION OF TWO OR MORE DRUGS IN A SINGLE DOSAGE FORM WHEREIN ONE OF THE DRUGS IS A PHYSOSTIGMINE COMPOUND

[75] Inventors: James B. Madison, Maryland Heights, Mo.; Larry K. Hiland, Edwardsville, Ill.

[73] Assignee: Chromalloy American Corporation, St. Louis, Mo.

[21] Appl. No.: 145,431

[22] Filed: May 1, 1980

[51] Int. Cl.$^3$ .................... A61K 31/44; A61K 31/40; A61K 31/33; A61K 31/46
[52] U.S. Cl. ................................. 424/263; 424/274; 424/244; 424/265; 424/267; 424/278; 424/330
[58] Field of Search .......................... 424/274, 10, 247

[56] References Cited
PUBLICATIONS

Rumack, Pediatrics, 52:3, (9/73), "Anticholinergic Poisoning: Treatment with Physostigmine," (3 pp.).
Manoguerra et al., J. Am. Col. of Emergency Physicians & Univ. Assoc. for Medical Emergency Services, 5:2, (2/76), pp. 125–127.
Walker et al., J. Am. Col. of Emergency Physicians & Univ. Assoc. for Medical Emergency Services, 5:6, (6/76), pp. 436–439.
Johnson, J. Am Col. of Emergency Physicians & Univ. Assoc. for Medical Emergency Services, 5:6, (6/76), pp. 443–445.
Smiler et al., Am. J. Obs. Gyn, 116:3, pp. 326–329, (1973).
Smith et al., J. Int'l Anesthesia Res. Soc., 55:4, (7/8–76), pp. 478–480.

*Primary Examiner*—Frank Cacciapaglia
*Attorney, Agent, or Firm*—Haverstock, Garrett & Roberts

[57] ABSTRACT

This invention relates to the combination of a physostigmine compound, including physostigmine, physostigmine salicylate, physostigmine sulfite, physostigmine sulfate and other esters and salts of physostigmine, in single dosage form, with one or more drugs that produce anticholinergia as an undesirable side effect, so that the physostigmine compound offsets the undesirable side effects, and makes a known drug or drugs, to which a physostigmine compound is added, safer and more desirable for patients to take. Physostigmine is also known as eserine.

14 Claims, No Drawings

COMBINATION OF TWO OR MORE DRUGS IN A SINGLE DOSAGE FORM WHEREIN ONE OF THE DRUGS IS A PHYSOSTIGMINE COMPOUND

PRIOR ART AND BACKGROUND OF THIS INVENTION

It is a well known fact that many effective drugs produce undesirable side effects. The use of prescription and non-prescription antihistamines often cause drowsiness, and, when taken along with other cold remedies, often cause dizziness and nausea. The effects of tranquilizers such as diazepam, and chlordiazepoxide often produce undesirable conditions such as instabilities. Pain killers such as propoxyphene and meperidine can cause drowsiness, dizziness, visual disturbances, tremors, uncoordinated muscle movements and so forth. Many drugs for treating ulcers often produce these same side effects. Mixing any of these drugs with alcohol is dangerous and may be even fatal.

Physostigmine was first isolated in 1864 by Jobst and Hesse after it was originally introduced into England in the form of the Calabar bean, in 1840, by Daniell, a British medical officer. During the last century, physostigmine has been used as a treatment for glaucoma and in post-operative ileus, and in the reversal of atropine-induced coma. More recently, physostigmine has been used effectively as an antidote to several drugs possessing central anticholinergic properties. See Journal Of The American College Of Emergency Physicians and University Association For Emergency Medical Services, June, 1976, Volume 5, Number 6, pages 436–439. Pediatrics, Volume 52, Number 3, September, 1973 discusses the use of physostigmine compounds such as physostigmine salicylate in the treatment of anticholinergic poisoning. The use of physostigmine in the treatment of anticholinergic poisoning is also discussed in Journal of The American College Of Emergency Physicians And University Association For Emergency Medical Services, Volume 5, Number 2, February, 1976, pages 125–127 wherein it is noted that drugs with anticholinergic effects are readily available to the public by prescription and over-the-counter and are increasingly the subject of abuse by the patients. This article discusses the use of physostigmine as an emergency antidote. The Journal Of The American College Of Emergency Physicians And University Association For Emergency Medical Services, Volume 5, Number 6, June, 1976, pages 443–445 also discusses the use of physostigmine in the treatment of tricylic antidepressant overdoses. The use of physostigmine compounds to reverse the effect of scopolamine in parturients is described in the American Journal of Obstetrics And Gynecology, Volume 116, Number 3, pages 326–329, June 1, 1976 and in The Journal Of International Anesthesia Research Society, Volume 55, Number 4, July-August, 1976. Thus, the use of physostigmine compound to counteract the undesirable anticholinergic effect of many useful drugs has been known for a number of years and is growing in utilization by physicians.

BRIEF DESCRIPTION OF THE INVENTION

Although the use of physostigmine compounds to counteract the anticholinergic effect of many useful drugs has been known since at least as early as 1968, this invention relates to the combination in a single dosage form of one or more useful drugs along with a physostigmine compound to provide a combination dosage whereby the desirable effects of a drug is enhanced by the immediate presence of a physostigmine compound which counters the anticholinergic effect of the drug without in any way inhibiting or adversely affecting the effect of the drug so that the patient never experiences the normal anticholinergic effect of the main drug.

Thus, it is a principal object of this invention to provide in a single dosage form, a combination of a drug known to produce anticholinergic effects with a physostigmine compound.

It is another object of this invention to provide in a single dosage form, a combination of a drug known to produce anticholinergic effects with a physostigmine compound selected from physostigmine and esters and salts of physostigmines.

It is a more specific object of this invention to combine in one dosage form a drug such as an antihistamine, an antidepressant, an antiparkinsonian drug, cold remedies, tranquilizers, antispasmodics and even alkaloids from natural products such as Jimson weeds along with a physostigmine compound such as physostigmine, physostigmine salicylate, physostigmine sulfite, and physostigmine sulfate.

Another object of this invention is to provide in a single dosage form an effective drug known to produce undesirable anticholinergic effects along with a physostigmine compound in the form of a tablet, powder, liquid, capsule, or an injectable solution.

A still more specific object of this invention is to combine in a single dosage form a physostigmine salicylate in an effective amount to counter the anticholinergic effects of any drug known to produce anticholinergia in animals who ingest a known drug which is known to produce anticholinergia.

DETAILED DESCRIPTION

Many well known drugs are known to produce undesirable anticholinergic effects or poisoning (in the case of overdose). The well known drug Elavil (amitriptyline) produces undesirable anticholinergia, and, when used in excess may produce coma. The use of Ornade Spansules (chlorpheniramine maleate isopropamide and phenylpropanolamine hydrochloride) often produces anticholinergia, including vomiting. In fact, almost all known prescriptions and over-the-counter antihistamines, antidepressants, antiparkinsonians, cold remedies, tranquilizers, antispasmodics and plants containing atropine-like alkaloids produce varying amounts of anticholinergia in almost all patients. Traditionally, when the indicated drugs are taken in recommended amounts, the anticholinergic effects wear off without harmful or adverse effects on the patients. Even though the anticholinergic side effect eventually dissipates such anticholinergic effects may result in non-health related problems. For example, a patient drowsy from taking antihistamines in recommended amounts, may become involved in an industrial accident or an automobile accident as a result of the anticholinergic effect of the ingested antihistamine. These problems are overcome by the use of this invention wherein a known drug in recommended amounts is combined in one dosage form with a physostigmine compound, which includes physostigmine, physostigmine salicylate, physostigmine sulfite, and physostigmine sulfate. Thus, this invention relates to the addition of physostigmine compounds to known drugs that are known to produce anticholinergia as an undesirable side effect so that the physostigmine off-sets these undesirable side effects, and makes a drug or drugs to which the physostigmine is added, safer and more desirable for patients to take.

Drugs known to produce anticholinergia include any prescription or over-the-counter drug which includes any one or more of the following drugs, such as amitriptyline
benztropine
brompheniramine
chlorpheniramine
desipramine
dimenhydrinate
diphenhydramine
doxepin
doxylamine
imipramine
nortriptyline
phenindamine
trihexyphenidyl
triprolidine Anticholinergia is defined as preventing the action of acetylcholine. Acteylcholine is defined as the acetic acid ester of choline, which is released and hydrolyzed during nerve conduction and muscle action by transmitting impulses across the nerve synapses. Physostigmine is defined as an alkaloid ($C_{15}H_{21}N_3O_2$), the active ingredient in Calabar beans. It has been used since 1877 to contract the pupil of the eye and in glaucoma.

Physostigmine is an alkaloid obtained from the Calabar bean having the following formula:

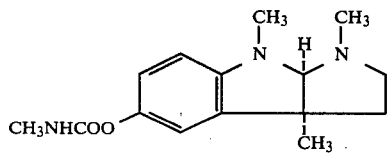

This invention covers the combination of two or more drugs in a single dosage form, which may be a capsule, tablet, powder, liquid, or injectable. One of the drugs is always physostigmine, or an ester or salt of physostigmine, which is generally recognized as safe and effective as an antagonist or antidote for anticholinergia. The second drug is any drug which has, as its specific function, an action other than to produce anticholinergia, but which does produce anticholinergia as a side effect. Various other drugs may be included in the combination, such as those generally used in combination with the second drug.

Examples of the above would include a combination of physostigmine salicylate with an antihistamine (such as chlorpheniramine maleate) which is used primarily to relieve the symptoms of rhinitis caused by allergies and the common cold. However, the antihistamine also causes anticholinergia which symptoms include drowsiness. Thus, the patient who takes the antihistamine by itself would be in danger of falling asleep while driving a car or operating machinery. The addition of physostigmine salicylate to the dosage form would off-set the drowsiness and make this drug safer to use generally. It is estimated that of all the population who take antihistamines about one-fourth to one-half are susceptible to the drowsiness effect of antihistamines.

This invention is then combining the known drugs, functioning in a clinically expected manner, which are known to cause anticholinergic effects, with physostigmine, or one of its esters or salts, which are known to be anticholinergic, into unitary dosage form, such as powders, capsules, tablets, liquids or injectables. Although the drugs function in a clinically expected manner, it is presently known only to use the antagonist for a drug displaying anticholinergic effect after the effect of the first drug becomes obvious.

The following table represents various useful combinations of known therapeutic drugs combined with a physostigmine compound:

TABLE ONE

| Useful Drug | Amt | Physostigmine Salicylate Amt. | Form |
| --- | --- | --- | --- |
| Chlorpheniramine Maleate | 2 mg. | 1 mg. | Tablet |
| Chlorpheniramine Maleate | 8 mg. | 4 mg. | T.D. * Capsule |
| Diphenhydramine HCL | 25 mg. | 1 mg. | Capsule |
| Dimenhydrinate | 50 mg. | 1 mg. | Injection |

*Enteric coated for time delay

EXAMPLE 1

A female human age 39 and weighing 110 pounds was prescribed Benadryl (diphenhydramine), a well known antihistamine in the amounts of 50 milligrams, 3 times per day. Following the prescribed amounts the first day on the drug, she found her mind was foggy, she became very sleepy, and had trouble orienting herself. The following day, while following the prescribed amounts of Benadryl she took a tablet comprised of the Benadryl and 1 milligram of physostigmine salicylate. Although the desired antihistaminic effect of the Benadryl continued, she experienced none of the side effects experienced on the previous day when the Benadryl was taken alone and not in combination with the physostigmine.

EXAMPLE 2

A solution containing one milligram of physostigmine salicylate, and two milligrams of chlorpheniramine maleate were combined in a syrup to form a five milliliter solution. This solution was ingested by 3 male humans and 3 female humans, all suffering from rhinitis, in a dosage of 5 milliliters every 4 hours. The rhinitis symptoms were almost immediately relieved in every subject and none of the subjects experienced any drowsiness normally associated with the use of antihistimine, chlorpheniramine.

EXAMPLE 3

A male human aged 60 and weighing 220 pounds was suffering from rhinitis caused by cigar and cigarette smoke. The rhinitis caused drainage from the nostrils and some coughing. The subject was given one tablespoon full of a water solution containing about 2 milligrams of Antilirium (a physostigmine salicylate marketed by O'Neal, Jones & Feldman division of Chromalloy American Corporation) and about 4 milligrams chlorpheniramine maleate in 10 milliliters of water. The results were immediate and dramatic. The rhinitis ceased and the subject suffered no drowsiness and remained alert and sharp.

The invention can be illustrated by various other combinations of physostigmine compositions and known drugs. Any of the other physostigmine compositions disclosed can be substituted for the physostigmine composition identified in examples 1–3 with similar results. Also, any of the known drugs disclosed in this specification can be substituted for the drugs disclosed in claims 1–3 with similar results.

The combinations of known drugs which produces an anticholinergic effect as a side effect to their main function and the physostigmine compound can be combined in a wide variety of proportions and will depend on the drug being used in the combination and the form provided for ingestion into a living animal body. The portions of known drugs in combination with physostigmine compounds in a single dosage form will be in conformance with the recommended dosage levels of these drugs as described in pharmaceutical compendia, such as "The Pharmacological Basis of Therapeutics" by Goodman and Gilman.

The useful amount of physostigmine compound ingested into the living animal body will generally be based on the amount of drug ingested to counter a particular symptom. The physostigmine compound will generally be ingested into a living animal body along with a known drug in an amount of 0.000001 to 0.000064 percent by weight of said living animal body.

The foregoing specification sets forth the preferred embodiments of my invention, however, it will be understood that any other adaptations of this invention are intended to be within the scope of this invention as set forth in the following claims.

What is claimed is:

1. A therapeutic composition comprising an antihistaminic drug selected from the group consisting of ethanolamine and alkylamine antihistaminic drugs which produce an anticholinergic effect combined in the same dose with a physostigmine compound selected from the group consisting of physostigmine, physostigmine salicylate, physostigmine sulfate and physostigmine sulfite in an amount effective to overcome the anticholinergic effect of the antihistaminic drug without inhibiting the antihistaminic effect.

2. A therapeutic composition according to claim 1 wherein said physostigmine compound is physostigmine.

3. A therapeutic composition according to claim 1 wherein said physostigmine compound is physostigmine salicylate.

4. A therapeutic composition according to claim 1 wherein said physostigmine compound is physostigmine sulfite.

5. A therapeutic composition according to claim 1 wherein said physostigmine compound is physostigmine sulfate.

6. A therapeutic composition according to claim 1 wherein said antihistaminic drug is chlorpheniramine and said physostigmine compound is physostigmine salicylate.

7. A therapeutic composition according to claim 1 wherein said antihistaminic drug and said physostigmine compound are combined in a water solution injectable dosage.

8. A therapeutic composition according to claim 1 wherein said antihistaminic drug and said physostigmine compound are combined in a compressed tablet.

9. A therapeutic composition according to claim 1 wherein said antihistaminic drug and said physostigmine compound are combined in a capsule.

10. A therapeutic composition according to claim 1 wherein said antihistaminic drug and said physostigmine compound are combined in a syrup.

11. A therapeutic composition according to claim 1 wherein said antihistaminic drug and said physostigmine compound are combined in a powder.

12. A therapeutic composition comprising from about one to about sixteen milligrams of a physostigmine compound selected from the group consisting of physostigmine, physostigmine salicylate, physostigmine sulfate and physostigmine sulfite combined in the same dose with from about one to about one hundred milligrams of an antihistaminic drug selected from the group consisting of ethanolamine and alkylamine antihistaminic drugs which produce anticholinergia.

13. A therapeutic composition comprising from about one to about sixteen milligrams of physostigmine salicylate combined in the same dose with from about one to about one hundred milligrams of an antihistaminic drug selected from the group consisting of ethanolamine and alkylamine antihistaminic drugs which produce anticholinergia.

14. A therapeutic composition comprising chlorpheniramine maleate which produces an anticholinergic effect combined in the same dose with physostigmine salicylate in an amount effective to overcome the anticholinergic effect of the chlorpheniramine maleate without inhibiting the antihistaminic effect.

* * * * *